United States Patent [19]
Han et al.

[11] Patent Number: 5,015,798
[45] Date of Patent: May 14, 1991

[54] CONVERSION OF METHANE

[75] Inventors: Scott Han, Lawrenceville, N.J.;
Robert E. Palermo, New Hope, Pa.;
Judy A. Pearson, Point Pleasant,
N.J.; Dennis E. Walsh, Richboro, Pa.

[73] Assignee: Mobil Oil Corporation, Fairfax, Va.

[21] Appl. No.: 454,532

[22] Filed: Dec. 21, 1989

[51] Int. Cl.$^5$ .................. C07C 2/00; C07C 5/327
[52] U.S. Cl. .................. 585/500; 585/658; 585/943
[58] Field of Search .................. 585/500, 658, 943

[56] References Cited

U.S. PATENT DOCUMENTS

| 3,965,205 | 6/1976 | Garwood et al. | 585/409 |
| 4,433,189 | 2/1984 | Young | 585/408 |
| 4,497,970 | 2/1985 | Young | 585/417 |
| 4,618,732 | 10/1986 | Gesser et al. | 568/910 |
| 4,695,663 | 9/1987 | Hall et al. | 585/500 |

FOREIGN PATENT DOCUMENTS 2070325  3/1987  Japan .................. 585/500

OTHER PUBLICATIONS

"Preparation of Aromatic Hydrocarbons From Methane In The Presence of $O_2$", by S. S. Shepelev and K. G. Ione, Mar. 22, 1983, pp. 323–325.
"Syntheses of Hydrocarbons From $C_1$ Compounds, Using Zeolite Catalysts", by S. S. Shepelev and K. G. Ione, 1984, pp. 284–288.
"Oxidation of Methane Over H-ZSM-5 and Other Catalysts", by J. R. Anderson & P. Tsai, 1985, pp. 141–152.
"The Effect of Oxygen on the Conversion of Light Paraffins on ZSM-5 Zeolites", by Gabriele Centi and Giorgio Golinelli, 1989, pp. 452–462.
"Oxidative Synthesis of Higher Hydrocarbons from Methane on Zeolites", by S. S. Shepelev and K. G. Ione, 1989, pp. 362–370.

Primary Examiner—W. J. Shine
Assistant Examiner—James Saba
Attorney, Agent, or Firm—Alexander J. McKillop; Charles J. Speciale; Edward F. Kenehan, Jr.

[57] ABSTRACT

There is provided a process for the direct partial oxidation of methane with oxygen, whereby organic compounds comprising higher hydrocarbons including $C_5+$ liquid hydrocarbons are produced. The catalyst used in this reaction may be a ZSM-5 catalyst. The process involves the use of an initial cofeed, such as propane, in admixture with the methane and oxygen to induce the formation of liquid hydrocarbons. As the reaction progresses, the flow of cofeed is shut off, and liquid hydrocarbons continue to be produced.

6 Claims, No Drawings

CONVERSION OF METHANE

CROSS-REFERENCE TO RELATED APPLICATION

This application is related to copending U.S. application Ser. No. 422,367 filed Oct. 16, 1989, the entire disclosure of which is expressly incorporated herein by reference.

BACKGROUND

There is provided a process for the direct partial oxidation of methane with oxygen, whereby organic compounds comprising liquid hydrocarbons are produced. The catalyst used in this reaction may be a ZSM-5 catalyst. The process involves the use of an initial cofeed, such as propane, in admixture with the methane and oxygen. The flow of the cofeed is shut off as the reaction progresses.

Natural gas is an abundant fossil fuel resource. Recent estimates places worldwide natural gas reserves at about $35 \times 10^{14}$ standard cubic feet, corresponding to the energy equivalent of about 637 billion barrels of oil.

The composition of natural gas at the wellhead varies but the major hydrocarbon present is methane. For example the methane content of natural gas may vary within the range of from about 40 to 95 vol. %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Processed natural gas, consisting essentially of methane, (typically 85-95 volume percent) may be directly used as clean burning gaseous fuel for industrial heat and power plants, for production of electricity, and to fire kilns in the cement and steel industries. It is also useful as a chemicals feedstock, but large-scale use for this purpose is largely limited to conversion to synthesis gas which in turn is used for the manufacture of methanol and ammonia. It is notable that for the foregoing uses no significant refining is required except for those instances in which the wellhead-produced gas is sour, i.e., it contains excessive amounts of hydrogen sulfide. Natural gas, however, has essentially no value as a portable fuel at the present time. In liquid form, it has a density of 0.415 and a boiling point of minus 162° C. Thus, it is not readily adaptable to transport as a liquid except for marine transport in very large tanks with a low surface to volume ratio, in which unique instance the cargo itself acts as refrigerant, and the volatilized methane serves as fuel to power the transport vessel. Large-scale use of natural gas often requires a sophisticated and extensive pipeline system.

A significant portion of the known natural gas reserves is associated with fields found in remote, difficulty accessible regions. For many of these remote fields, pipelining to bring the gas to potential users is not economically feasible.

Indirectly converting methane to methanol by steam-reforming to produce synthesis gas as a first step, followed by catalytic synthesis of methanol is a well-known process. Aside from the technical complexity and the high cost of this two-step, indirect synthesis, the methanol product has a very limited market and does not appear to offer a practical way to utilize natural gas from remote fields. The Mobil Oil Process, developed in the last decade provides an effective means for catalytically converting methanol to gasoline, e.g. as described in U.S. Pat. No. 3,894,107 to Butter et al. Although the market for gasoline is huge compared with the market for methanol, and although this process is currently used in New Zealand, it is complex and its viability appears to be limited to situations in which the cost for supplying an alternate source of gasoline is exceptionally high. There evidently remains a need for other ways to convert natural gas to higher valued and/or more readily transportable products.

A reaction which has been extensively studied for many years is the direct partial oxidation of methane to methanol. This route, involving essentially the reaction of methane and gaseous oxygen according to the simple equation $$CH_4 + \tfrac{1}{2} O_2 \rightarrow CH_3OH$$

could theoretically produce methanol with no by-product. The homogeneous reaction of methane with oxygen to produce methanol occurs most favorably under high pressure (10 to 200 atm.), moderate temperatures, (350°-500° C.), and at relatively low oxygen concentration. Oxidation to formaldehyde and deep oxidation reactions are minimized under these conditions. The mechanism of methanol formation is believed to involve the methylperoxy radical ($CH_3OO\cdot$) which abstracts hydrogen from methane. Unfortunately, the per pass yields have been limited. This limited yield has been rationalized as resulting from the low reactivity of the C-H bonds in methane vis-a-vis the higher reactivity of the primary oxygenated product, methanol, which results in selective formation of the deep oxidation products CO and $CO_2$ when attempts are made to increase conversion.

U.S. Pat. No. 4,618,732 to Gesser et al. describes an improved homogeneous process for converting natural gas to methanol. The alleged high selectivity for methanol is ascribed by the inventors to careful premixing of methane and oxygen and to eliminating reactor wall effects by use of glass-lined reactors.

Shepelev and Ione (React. Kinet. Catal. Lett., 1983, 23,323), found that mixtures of oxygen and methane in the presence of certain zeolites leads mainly to the formation of CO, $CO_2$ and $H_2O$ at 600° C. and atmospheric pressure. It appeared possible, however, to detect traces of ethane, ethylene, hydrogen and benzene. Studies at 100 atmosphere pressure and 400° C. indicated that a small amount of (unspecified) higher hydrocarbons formed. The methane and oxygen used were of 99.9% purity and reported free of higher hydrocarbons. However, U.S. Pat. No. 4,497,970 to D. Young discloses that such mixtures passed over zeolites under conditions similar to those used by Shepelev and Ione (Ibid) formed only carbon oxides and water.

SUMMARY

There is provided a process for synthesizing a mixture of organic compounds comprising liquid hydrocarbons by the direct partial oxidation of methane, said process comprising the steps of:

(i) preparing a feed mixture comprising methane, oxygen gas, and a reaction modifier having at least two carbon atoms, said reaction modifier being selected from the group consisting of hydrocarbons, oxygenated hydrocarbons and mixtures thereof, said feed mixture containing about 3 to about 30 volume percent $O_2$ and an amount up to about 5 volume percent of said reaction modifier, said amount being effective to induce formation of said liquid hydrocarbons;

(ii) contacting said feed mixture with an intermediate pore size crystalline aluminosilicate zeolite catalyst having a silica to alumina ratio of at least about 12, said contacting being conducted under a combination of conversion conditions including a temperature of about 350° to about 500° C., a gas hourly space velocity (GHSV) on zeolite of about 100 to 100,000 $hr^{-1}$, and a pressure of about 150 to about 3000 psig;

(iii) recovering said mixture of organic compounds comprising liquid hydrocarbons;

(iv) removing said reaction modifier from said feed mixture, thereby discontinuing the contact of said reaction modifier with said catalyst, while continuing the contact of said methane and oxygen gas with said catalyst; and (v) continuing to recover said mixture of organic compounds comprising liquid hydrocarbons.

The above-mentioned steps (i), (ii), and (iii) correspond to steps set forth in the aforementioned U.S. application Ser. No. 422,367, filed Oct. 16, 1989. It has surprisingly been discovered that the flow of the reaction modifier over the catalyst can be interrupted, which still producing liquid hydrocarbons.

It will be understood that the expression, higher hydrocarbons, as used herein, means hydrocarbons which have more carbon atoms (i.e. at least 2 carbon atoms) than methane. It will be further understood that the expression $C_5+$ liquid hydrocarbons, as used herein, means liquid hydrocarbons which have at least 5 carbon atoms. It will be further understood that oxygenated hydrocarbons are organic compounds composed of hydrogen, carbon and oxygen. Examples of such oxygenated hydrocarbons include alcohols (especially monohydric alcohols), aldehydes, ketones and ethers. Examples of hydrocarbons which may be used as reaction modifiers include paraffins, olefins and aromatics.

EMBODIMENTS

The catalysts useful herein comprise a type of zeolite termed herein as an intermediate pore size zeolite. These particular zeolites are also known as zeolites which have a Constraint Index of from 1 to 12.

The members of the class of zeolites useful herein have an effective pore size of generally from about 5 to about 8 angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolite ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 angstroms. On the other hand, zeolites which provide relatively free access to the internal zeolite structure have a low value for the Constraint Index, and usually pores of large size, e.g. greater than 8 angstroms. The method by which Constraint Index is determined is described fully in U.S. Pat. No. 4,016,218, incorporated herein by reference for details of the method.

Constraint Index (CI) values for same typical materials are:

|  | CI (at test temperature) |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-38 | 2 (510° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index provides a definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of interest herein within the approximate range of 1 to 12.

In the practice of the present invention, it is preferred to use a dual flow system, i.e., a system in which the natural gas and the oxygen or air are kept separate until mixed just prior to being introduced into the reactor. However, if desired, the oxygen and natural gas may be premixed and stored together prior to the reaction. The preferred dual flow system minimizes the risk of fire or explosion. In the dual flow system, the amount of oxygen flow is controlled so as to prepare a reaction mixture that contains 2 to 20 percent by volume, more preferably 3 to 15 percent of oxygen. Air may be used instead of oxygen without affecting the reaction. The gas hourly space velocity (GHSV) on zeolite is within the range of about 100 to 100,000 hr $^{-1}$, preferably about 1,000 to 10,000 hr $^{-1}$, and more preferably about 2,000 to 8,000 hr $^{-1}$.

The temperature in the reaction zone is from about 300° C. to 500° C., and preferably about 350° C. to 475° C. In the preferred mode of operation, the reactor temperature is increased until substantially all of the oxygen is consumed by the reaction, i.e., greater than about 90 percent oxygen consumption, and then it is held at about that temperature until further adjustment is required.

The pressure in the reaction zone may be from 150 to 3000 psig.

COMPARATIVE EXAMPLES A AND B

For these Comparative Examples an (H)ZSM-5 catalyst having a silica to alumina ratio of 70:1 was mixed with alumina (65% zeolite, 35% binder) and formed into extrudate. The extrudate (8.0 cc), ground to 20-40 mesh, was mixed with an equal volume of sand and loaded into the reactor's 9/16 inch I.D. pyrex glass liner.

In these Comparative Examples feed mixtures were prepared from ultra high purity methane (composition shown in Table I) and C.P. grade oxygen supplied by Matheson, and the feed, with no reaction modifier, was passed over (H)ZSM-5 catalyst. The oxygen contents differed in Comparative Examples A and B, as did the total pressure and space velocities. These differences and the results of the experiments are included in Table II. It is evident from the data in Table II that methanol was the sole useful product, and that the presence of the (H)ZSM-5 in Comparative Example A did not result in higher hydrocarbon production. The more severe conversion conditions of Comparative Example B resulted in small amounts of $C_2$-$C_4$ hydrocarbons being formed, but in neither Comparative Example was liquid hydrocarbon detected.

TABLE I

| Composition (vol. %) of Methane/$N_2$ Primary Standard | |
|---|---|
| Component | Methane/$N_2$ Primary Standard |
| $CH_4$ | 97.91 |
| Ethane | — |
| Propane | — |
| Butanes | — |
| $C_5$'s | — |
| $CO_2$ | — |
| $N_2$ | 2.09 |
| $H_2$ | — |
| | 100.00 |

TABLE II

| METHANE CONVERSION OVER ZSM-5 | | |
|---|---|---|
| Comparative Example No. | A | B |
| Catalyst | ZSM-5 | ZSM-5 |
| Temp., °C. | 450 | 450 |
| Pressure, psig | 960 | 1400 |
| $C_3$ Type | — | — |
| $C_3$ Conc., vol % | — | — |
| $O_2$ Conc., vol % | 7.0 | 12.7 |
| GHSV, hr$^{-1}$ (zeo) | 4600 | 3300 |
| $CH_4$ Conv., % | 5.2 | 8.8 |
| $C_3$ Conv., % | — | — |
| $O_2$ Conv., % | 100 | 100 |
| Total Carbon Conv., % | 5.2 | 8.8 |
| Product Selectivities (Based on Total Converted Carbon) | | |
| CO, % | 43.1 | 52.2 |
| $CO_2$ % | 40.2 | 36.4 |
| $CH_3OH$, % | 16.7 | 1.1 |
| Other Aq. Phase Oxygenates, % | — | 2.9 |
| $C_2$'s, % | — | 2.4 |
| $C_4$'s, % | — | 5.0 |
| Liquid HC Product, % | — | — |
| $C_2$-$C_4$ Yield, % | — | 0.7 |
| Liquid HC Yield, % | — | — |

EXAMPLE

The experimental procedures used in this Example were the same as those used in the Comparative Examples. Two HZSM-5 catalysts, with molar $SiO_2$/$Al_2O_3$=1000/1 and 26/1, were used. Both catalysts were 65 wt% zeolite physically mixed with 35% alumina, pelleted and meshed to size.

Catalytic data and results are given in Table III. Run 1 was carried out with propane co-feed over fresh 1000/1 ZSM-5 and run 2 was the same run over the catalyst used in run 1 but with the propane co-feed turned off. Run 3 was carried out with propane co-feed over fresh 26/1 ZSM-5 and run 4 was the same run over the catalyst used in run 3 but with the propane co-feed turned off. The data in Table III show that conversions and selectivities, particularly $C_5$+ hydrocarbon selectivities, are similar after the flow of the propane reaction-modifier has been turned off.

TABLE III

| Catalytic Data and Results. | | | | |
|---|---|---|---|---|
| Run | 1 | 2 | 3 | 4 |
| Catalyst | ZSM-5 | ZSM-5 | ZSM-5 | ZSM-5 |
| $SiO_2$/$Al_2O_3$ | 1000/1 | 1000/1 | 26/1 | 26/1 |
| Pressure, psig | 960 | 960 | 960 | 960 |

TABLE III-continued

| Catalytic Data and Results. | | | | |
|---|---|---|---|---|
| Run | 1 | 2 | 3 | 4 |
| Temp., °C. | 450 | 465 | 450 | 450 |
| GHSV (zeolite), hr$^{-1}$ | 4600 | 4600 | 4600 | 4600 |
| Feed | | | | |
| $CH_4$, % | 92.3 | 92.5 | 93.0 | 93.1 |
| $C_3$, % | 0.4 | — | 0.4 | — |
| $O_2$, % | 7.3 | 7.5 | 6.6 | 6.9 |
| Feed carbon conversion, % | 5.6 | 5.8 | 5.9 | 5.4 |
| Selectivities, % | | | | |
| $CO_x$ | 87.1 | 84.8 | 82.9 | 82.7 |
| Oxygenates | 1.3 | 0.4 | 2.9 | 1.6 |
| $C_2$-$C_4$ | 3.6 | 6.7 | 2.9 | 5.4 |
| $C_5+$ | 8.0 | 8.1 | 11.3 | 10.3 |

What is claimed is:

1. A process for synthesizing a mixture of organic compounds comprising higher hydrocarbons including $C_5+$ liquid hydrocarbons by the direct partial oxidation of methane, said process comprising the steps of:
   (i) preparing a feed mixture comprising methane, oxygen gas, and a reaction modifier having at least two carbon atoms, said reaction modifier being selected from the group consisting of hydrocarbons, oxygenated hydrocarbons and mixtures thereof, said feed mixture containing about 3 to about 30 volume percent $O_2$ and an amount up to about 5 volume percent of said reaction modifier, said amount being effective to induce formation of said liquid hydrocarbons;
   (ii) contacting said feed mixture with an intermediate pore size crystalline aluminosilicate zeolite catalyst having a silica to alumina ratio of at least about 12, said contacting being conducted under a combination of conversion conditions including a temperature of about 350° to about 500° C., a gas hourly space velocity on zeolite of about 100 to 100,000 hr$^{-1}$ and a pressure of about 150 to about 3000 psig;
   (iii) recovering said mixture of organic compounds comprising liquid hydrocarbons;
   (iv) discontinuing said reaction modifier from said feed mixture, thereby discontinuing the contact of said reaction modifier with said catalyst, while continuing the contact of said methane and oxygen gas with said catalyst; and
   (v) continuing to recover said mixture of organic compounds comprising liquid hydrocarbons.

2. A process according to claim 1, wherein said catalyst comprises HZSM-5.

3. A process according to claim 1, wherein said temperature is at least the minimum temperature required for substantially complete consumption of said oxygen.

4. A process according to claim 3, wherein said temperature is about 25° C. higher than said minimum temperature.

5. A process according to claim 1, wherein said modifier is selected from the group consisting of paraffins, olefins, aromatics and monohydric alcohols.

6. A process according to claim 1, wherein said modifier is propane or propylene.

* * * * *